US007129366B2

(12) United States Patent
Yang

(10) Patent No.: US 7,129,366 B2
(45) Date of Patent: Oct. 31, 2006

(54) GROUP OF A NOVEL ANTI-CANCER COMPOUNDS WITH SPECIFIC STRUCTURE

(75) Inventor: Zhenhua Yang, West Covina, CA (US)

(73) Assignee: Yang's Biochem Co. Ltd., Diamond Bar, CA (US)

( * ) Notice: Subject to any disclaimer, the term of this patent is extended or adjusted under 35 U.S.C. 154(b) by 0 days.

(21) Appl. No.: 10/485,103

(22) PCT Filed: Aug. 2, 2002

(86) PCT No.: PCT/US02/24296

§ 371 (c)(1),
(2), (4) Date: Feb. 2, 2004

(87) PCT Pub. No.: WO03/014296

PCT Pub. Date: Feb. 20, 2003

(65) Prior Publication Data

US 2004/0204599 A1 Oct. 14, 2004

Related U.S. Application Data

(60) Provisional application No. 60/309,487, filed on Aug. 3, 2001.

(51) Int. Cl.
*C07C 57/00* (2006.01)
(52) U.S. Cl. ............... 554/224; 514/558; 514/559; 514/675; 514/693; 514/724; 562/433; 562/553; 568/303; 568/579; 568/700
(58) Field of Classification Search ............ 554/224; 568/303, 579, 700; 514/558, 559, 675, 693, 514/724; 562/433, 553
See application file for complete search history.

(56) References Cited

U.S. PATENT DOCUMENTS 6,214,875 B1  4/2001  Yang

FOREIGN PATENT DOCUMENTS

CA   2 286 750       4/2000
JP   11-049767   *   2/1999
WO   01/59067         8/2001

OTHER PUBLICATIONS

Chem. Abstr. of RU 2177699, Jun. 2000.*
Ihn et al.,Chem. Abstr. of "On the structure of streptovirudin", Tetrahedron, vol. 38(12), pp. 1781-1785, 1982.*
Chem. Abstr. of CN-1,282,730, Yang, 7-200.*
Larsson et al., "Antimicrobial effect of simlpe lipids with different branches at the methyl end group",Antimicrobial Agents and Chemotherapy, 8(6), pp. 742-750, 1975.*
Buu-Hoi et al, Preparation d' acides gras iso et gem—dialcoyles par hydrogenolyse sedulfurante de dervies du thiophene, Bulletin De La Societe Chimque De France, (12), pp. 3640-3643, 1965.*
Jacob et al, "The structure of preen gland waxes from pelecaniform birds containing 3,7,-dimethy;octan-1-ol. An active ingredient against dermatophytes", Zeitschrift Fuer Naturforschung, C:Biosciences, 52(½), pp. 114-123, 1997.*
Database CA 'Online!, AN 2002:14691, XP-002356944, CN 1282730, Feb. 7, 2001.
Kare Larsson, et al., "Antimicrobial Effect of Simple Lipids with Different Branches at the Methyl End Group", Antimicrobial Agents and Chemotherapy, vol. 8, No. 6, XP-002356941, 1975, pp. 742-750.
N. P. Buu-Hoi, et al., "Preparation d'acides gras iso et gem-dialcoyles par hydrogenolyse desulfurante de derives du thiophene", Bulletin de la Societe Chimique de France, XP-008056596, 1965, pp. 3640-3643.
Database CA 'Online!, AN 2003:360163, XP-002356945, CN 1343650, Apr. 10, 2002.
W. Ihn, et al., "Zur Chemischen Struktur Der Streptovirudine-1, Säurehydrolytischer Abbau Und Konstitution Der Gebildeten Fettsäuren", Tetrahedron, vol. 38, No. 12, XP-001208007, 1982, pp. 1781-1785 (with English Abstract).
Jürgen Jacob, et al., "The Structure of Preen Gland Waxes from Pelecaniform Birds Containing 3,7-Dimethyloctan-1-ol-an Active Ingredient Against Dermatophytes", Biosciences, 52(½), XP-008056570, 1997, pp. 114-123.

* cited by examiner

*Primary Examiner*—Deborah D. Carr
(74) *Attorney, Agent, or Firm*—Oblon, Spivak, McClelland, Maier & Neustadt, P.C.

(57) ABSTRACT

Compounds containing a specific saturated or unsaturated branched chain terminal group; a polar leading group; and a long-chain aliphatic, non-cyclic, saturated or unsaturated, substituted or unsubstituted, hydrocarbon group linking them; and having anti-cancer, immunosuppression alleviation, immune boosting and anti-inflammation activity.

12 Claims, No Drawings

GROUP OF A NOVEL ANTI-CANCER COMPOUNDS WITH SPECIFIC STRUCTURE

This application claims the benefit of U.S. Provisional Application 60/309,487, filed Aug. 3, 2001, which application is hereby incorporated by reference.

BACKGROUND OF THE INVENTION

1. Field of the Invention

The invention is drawn to a group of compounds with specific structure, which possess anti-cancer activity. It also relates to their use in human and other mammalian subjects for cancer therapy, prevention, and immune boosting and inflammation functions.

2. Description of the Background

JP-A 04295423 and JP-B 07072134, each to Daiichi, disclose anti-cancer agents containing MeCHR(CH2)nCOOH wherein R is C1–C5 alkyl and n=4–22. U.S. Pat. No. 4,985,466 to Deguchi disclose a method for treating tumor susceptible to treatment with a wool fatty acid, or its reduced alcohol, metal salt or aliphatic ester derivative, or a wool alcohol, or its carboxylic acid, aliphatic ether or aliphatic ester derivative. Deguchi additionally disclose that it is characteristic of wool fatty acid and wool alcohol to contain a large quantity of iso- and anteiso-higher saturated aliphatic acids and alcohols.

However, none of the above prior art recognizes Applicant's discovery that the anti-cancer activity resides in a terminal branch structure and a leading end group per se directly linked at opposite ends, respectively, to a long chain group.

A group of specific iso- and anteiso-branched-chain fatty acids with significant anti-cancer effect has been described in Applicant's U.S. Pat. No. 6,214,875. Such compounds as described in the above Applicant's U.S. patent, and derivatives thereof obtained by reacting the acid moiety thereof, are described in Applicant's U.S. application Ser. No. 09/647,918, which is a 371 application of PCT/US99/06525, filed Apr. 14, 1999, and which was published as WO 99/53086 on Oct. 21, 1999, which WO 99/53086 is hereby incorporated by reference.

These compounds have shown excellent cytotoxic activity through induction of apoptosis against a broad variety of cancer cells, including, but not limited to, leukemia, breast cancer, prostate cancer, lung cancer, with extremely low toxicity to experimental animals.

Applicant's WO 01/59067 describes a group of anti-cancer compounds which are comprised of three parts: an end-terminal group, which is isopropyl, sec.-butyl, or tert.-butyl group; a leading group; and a long-chain aliphatic, non-cyclic, saturated or unsaturated, hydrocarbon group that links the end-terminal group and the leading group.

This specific group of compounds, described in WO 01/59067 is illustrated by the following three formulae (1), (2) or (3):

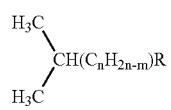

(1)

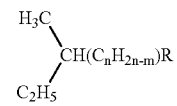

(2)

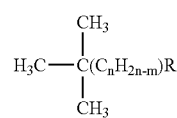

(3)

wherein n is an integer of at least 5, m is an even integer from 0 to 2b, inclusively, wherein b is the maximum number of unsaturated bonds on the long chain (a double bond is assigned as 1 and a triple bond is assigned as 2), and R can be any polar group.

SUMMARY OF THE INVENTION

In the present invention, this specific group of compounds can be further illustrated by the following typical structural formulae (4) through (12), and include their possible pharmaceutically acceptable salts:

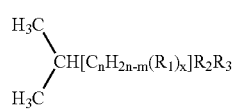

(4)

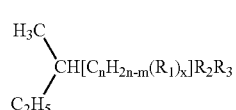

(5)

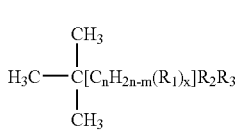

(6)

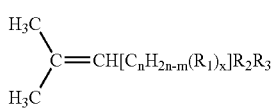

(7)

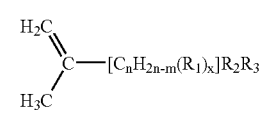

(8)

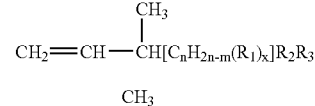

(9)

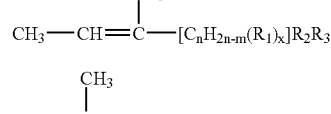

(10)

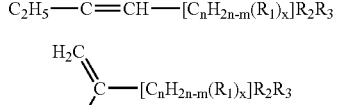

(11)

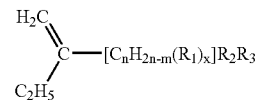

(12)

wherein n is an integer between 5 to 19, m is an integer from 0 to 2b+x, inclusively, wherein b is the maximum number of unsaturated bonds (a double bond is assigned as 1 and a triple bond is assigned as 2), $R_1$, $R_2$, $R_3$ are any groups that are chemically allowed in the above formulae, provided that $R_2R_3$ is a polar moiety. x represents the number of groups $R_1$ (x is an integer $\leq 2n-m$), which groups can be the same or different, and can be connected at the α-carbon or at any other possible position. In other words, hydrogen(s) may be replaced with $R_1$ in the $C_nH_{2n-m}$ moiety up to the total number of available hydrogens. It is understood that both hydrogens on a carbon atom may be replaced with a single divalent group, such as oxo.

However, to the extent $R_1$, $R_2$, and $R_3$ include groups resulting in compounds disclosed by Daiichi or Deguchi, supra, or other prior art, these compounds are excluded herein from the compounds claimed. Thus, excluded are compounds of formulae (4) and (5) wherein m=0, x=0, and $R_2R_3$ is —COOH or an aliphatic ester thereof or salt thereof, or $R_2R_3$ is —OH or an aliphatic ether thereof or aliphatic ester thereof.

DETAILED DESCRIPTION OF THE INVENTION

It should be presumed below that any differences between a chemical structure and its chemical name be resolved in favor of the chemical structure.

In the present invention, $R_1$ can be, but is not limited to, the following:

(1) hydrogen, —H

EXAMPLES

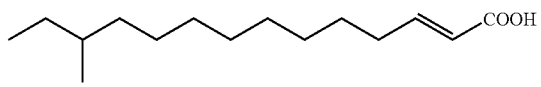

12-Methyl-2-tetradecenoic acid,

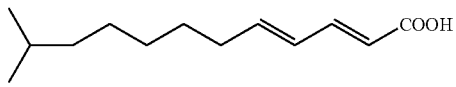

11-Methyl-dodeca-2,4-dienoic acid,

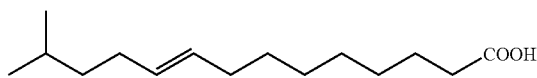

13-Methyl-9-tetradecene acid,

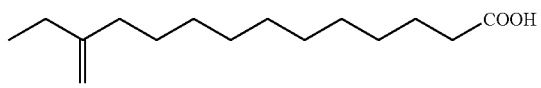

12-Ethyl-12-tridecenoic acid;

(2) methyl group, —CH₃

EXAMPLE

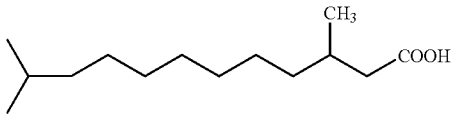

3,11-Dimethyl-dodecanoic acid;

(3) ethyl group, —C₂H₅

EXAMPLES

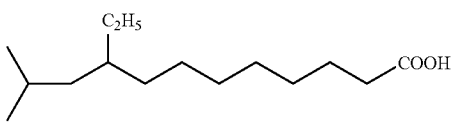

9-Ethyl-11-methyl-dodecanoic acid;

(4) hydroxyl group, —OH

EXAMPLE

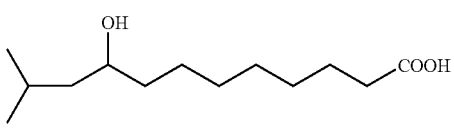

9-Hydroxy-11-methyl-dodecanoic acid;

(5) amino group, —NH₂

EXAMPLE

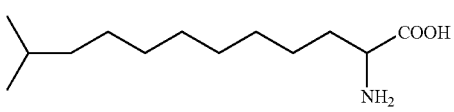

2-Amino-11-methyl-dodecanoic acid;

(6) mercapto group, —SH

EXAMPLE

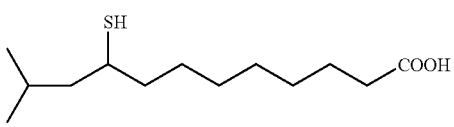

9-Mercapto-11-methyl-dodecanoic acid;

(7) oxo group, =O

EXAMPLE

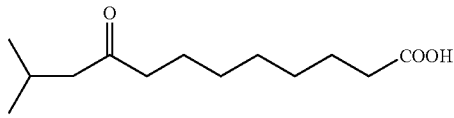

9-Oxo-11-methyl-dodecanoic acid;
(8) imino group, =NH, or hydroxyimino, =N—OH

EXAMPLE

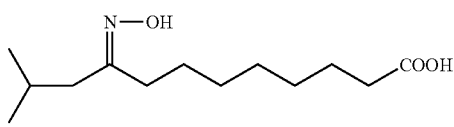

9-Hydroxyimino-11-methyl-dodecanoic acid;
(9) halogen

EXAMPLE

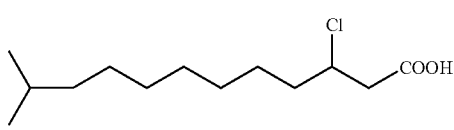

3-Chloro-11-methyl-dodecanoic acid;
(10) amino acid

EXAMPLE

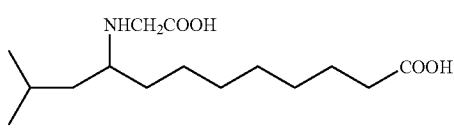

9-Carboxymethylamino-11-methyl-dodecanoic acid;
(11) amino-glucose

EXAMPLE

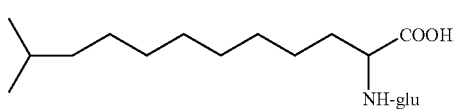

2-Glucosamino-11-methyl-dodecanoic acid;

(12) heterocyclic ring or substituted heterocyclic

EXAMPLE

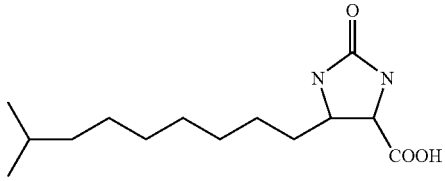

4-(8-Methyl-nonyl)-5-carboxy-tetrahydroimidazoyl-2-one,

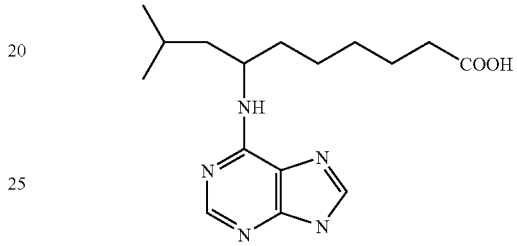

7-(6N-Adenyl)-9-methyl-decanoic acid.

The above group or structure can be in any position of the carbon chain and the number of such group or structure is x, (x is an integer≦2n−m), which can be the same or different.

$R_2$ can be, but is not limited to, the following:
(1) alkoxylene group, —CH$_2$O

EXAMPLE

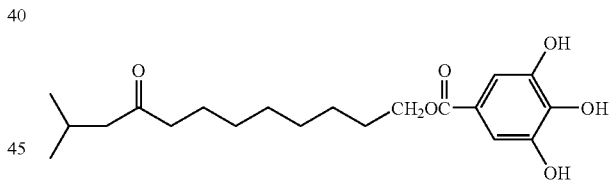

11-Methyl-9-oxo-dodecyl (3,4,5-trihydroxy)benzoate;
(2) carbonyl group,

EXAMPLE

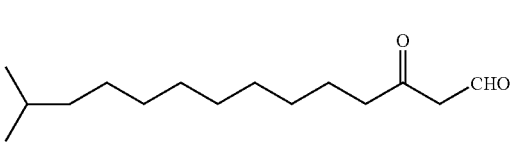

13-Methyl-3-oxo-tetradecanal,

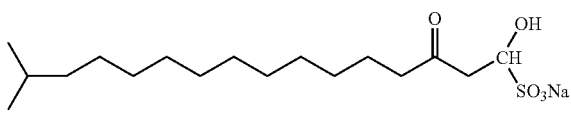

Sodium 15-methyl-3-oxo-1-hydroxy-hexadecylsulfonate,

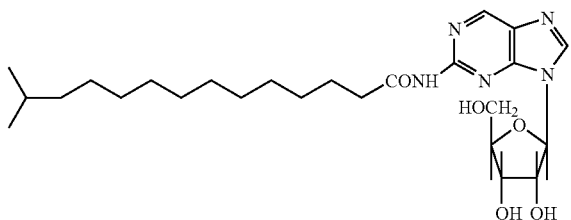

N-(-13-Methyl-tetradecanoyl)-2-amino-7-ribo purine,

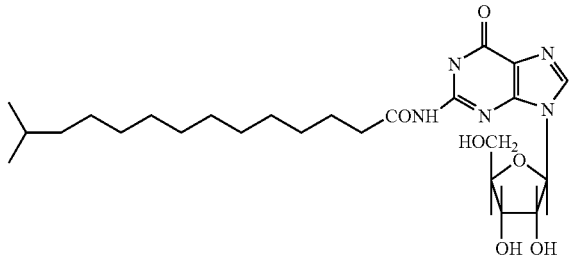

2N-(13-Methyl-tetradecanoyl)-guanosine,

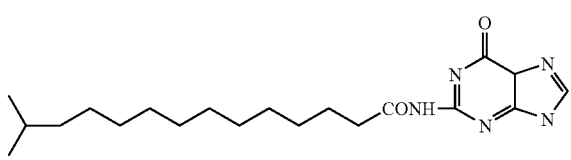

2N-(13-Methyl-tetradecanoyl)guanine,

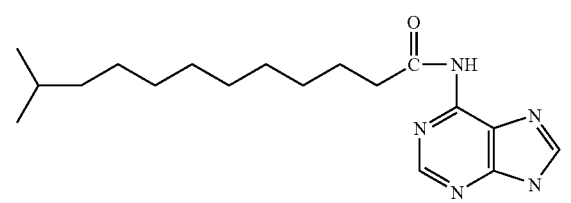

6N-(11-Methyl-dodecanoyl)adenine;

(3) amine group,

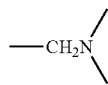

EXAMPLE

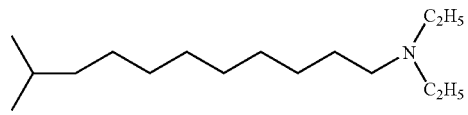

N,N-Diethyl-10-methylundecylamine,

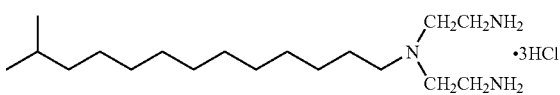

N,N-di(2-aminoethyl)-12-methyl-tridecylamine tri-hydrochloride;

(4) imine group, —C=N—

EXAMPLE

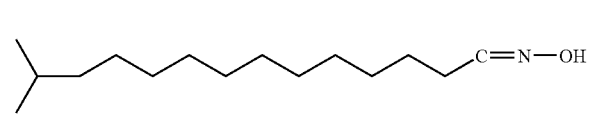

13-Methyl-tetradecanal-N-hydroxyimine,

N-4-Carboxy-benzyl-(11-methyl-3-oxo-dodecyl)imine;

(5) substituted or unsubstituted phenyl group, or substituted or unsubstituted heterocyclic group

EXAMPLE

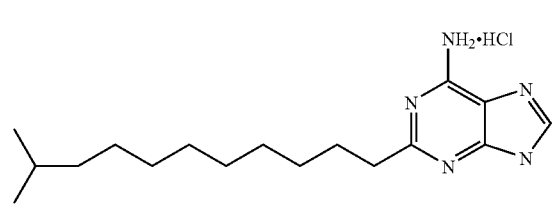

2-(10-Methyl-undecyl)-adenine hydrochloride,

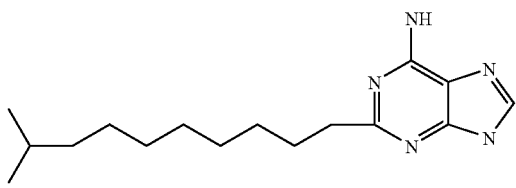

2-(9-Methyl-decyl)-adenine,

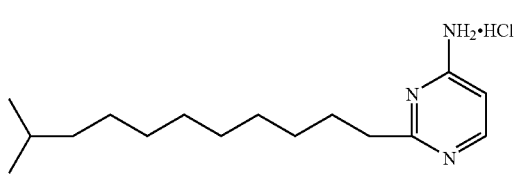

2-(11-Methyldodecyl)-4-amino-pyrimidine hydrochloride.

$R_3$ is any possible group connecting with $R_2$ so that $R_2R_3$ is a polar group. It can be, but is not limited to, the following:

(1) hydrogen, —H

EXAMPLE

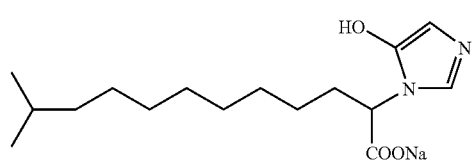

Sodium 2-(5-hydroxy-1-imidazolyl)-11-methyl-dodecanoate;

(2) hydroxyl group, —OH

EXAMPLE

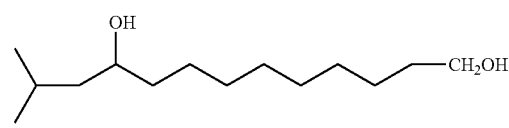

12-methyl-1,10-tridecanediol,

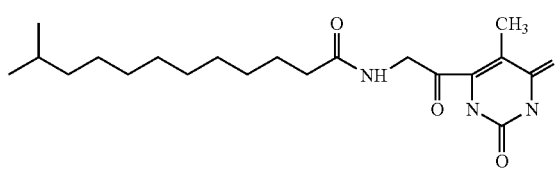

6-[(N-11-Methyl-dodecanoyl)glycyl]thymine;

(3) amine group,

EXAMPLE

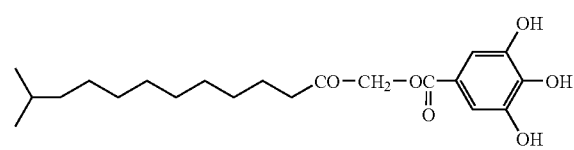

13-Methyl-tetradecyl urea;

(4) methyl group, —CH$_3$, or ethyl group, —C$_2$H$_5$

EXAMPLE

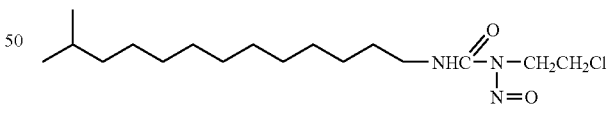

(11-Methyl-9-hydroxy-dodecyl)ethyl ether;

(5) acyl group, —COR$_4$

EXAMPLE

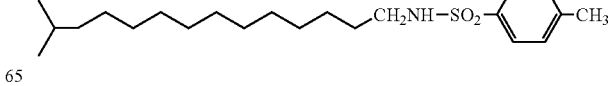

12-Methyl-3-oxo-tridecyl-3,4,5-trihydroxy benzoate,

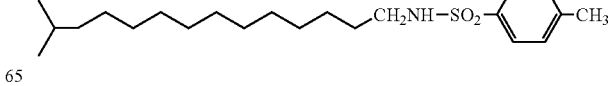

1-(2-Chloroethyl)-1-nitroso-3-(12-methyl-tridecyl)urea;

(6) sulfonyl group, —SO$_2$R$_4$

EXAMPLE

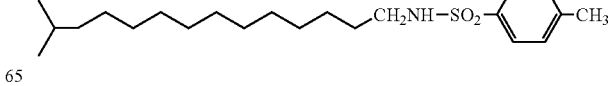

N-4-Methyl-benzenesulfonyl-13-Methyl-tetradecyl amine;

(7) hydroxyl-, halogen-, halide-, carboxyl-, carbonyl-, amino-, or glucosyl-substituted phenyl group or heterocyclic group.

EXAMPLE

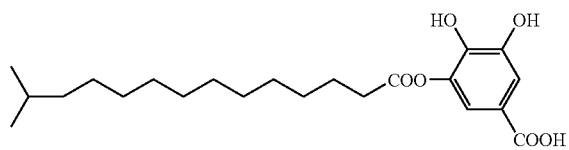

(5-Carboxy-2,3,-dihydroxy phenyl)13-methyl-tetradecanoate,

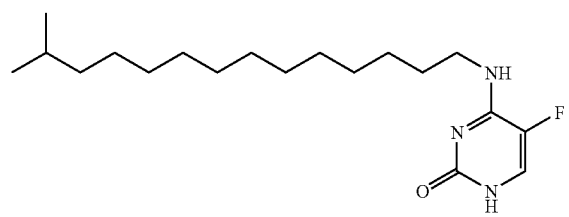

6N-13-methyl-tetradecyl-5-flucytosine,

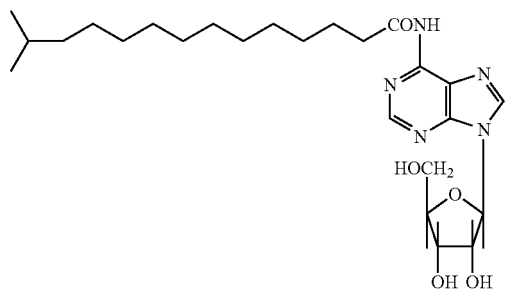

6N-(13-Methyl-tetradecanoyl)adenosine,

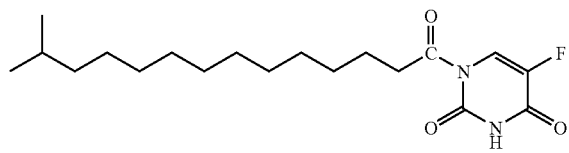

1N-(13-methyl-tetradecanoyl)-5-fluoropyrimidine-2,4-dione,

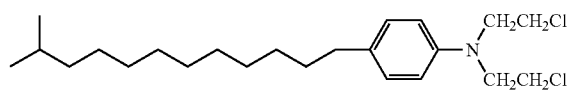

N,N-Di(2-chloroethyl)-4-(13-methyl-tetradecyl)aniline,

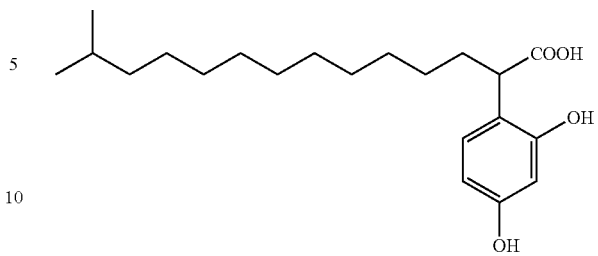

2-(2,4-Dihydroxyphenyl)-13-methyl tetradecanoic acid;

(8) hydrazine group

EXAMPLE

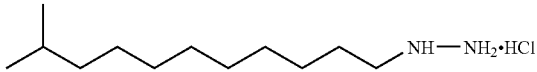

N-(12-methyl-tridecyl)hydrazine hydrochloride.

The $R_4$ and $R_5$ groups in the above structures can each independently be, but are not limited to, the following: hydrogen, methyl, ethyl, chloroethyl, ethoxyl, hydroxyl-, halogen-, halide-, carboxyl-, carbonyl-, amino-, or glucosyl-substituted phenyl group or heterocyclic group. $R_4$ and $R_5$ can also form a heterocyclic ring such as piperidine, pyrrolidine or morpholine.

In the structure of the above compounds, the hydrogen(s) in any hydroxyl group (—OH) or amine group (—NH$_2$), whether on an aliphatic chain or phenyl ring, can be replaced with a substituent to form, for example, methoxy (—OCH$_3$), ethyloxy (—OC$_2$H$_5$), or acetyloxy (—OCOCH$_3$)group.

EXAMPLES

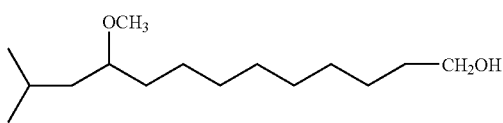

10-Methoxy-12-methyl-tridecanol,

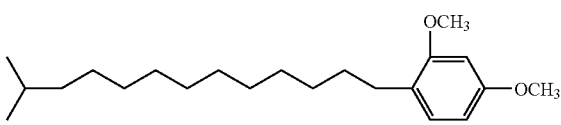

(12-Methyl-tridecyl)-2,4-dimethoxy benzene,

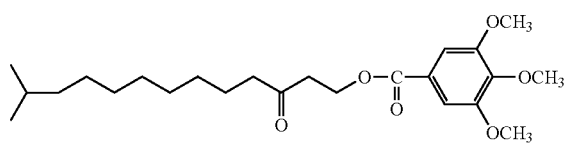

12-Methyl-3-oxo-tridecyl-3,4,5-trimethoxy-benzoate,

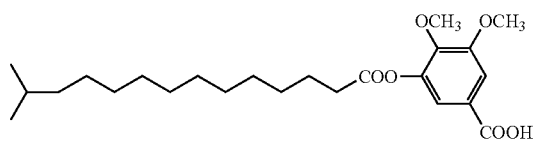

(5-Carboxy-2,3-dimethoxyphenyl)13-methyl-tetradecanoate.

The anti-cancer compounds described in the present invention can be chemically synthesized routinely.

Experiment 1 In vitro Anti-Cancer Efficacy

The following 49 compounds with specific structure according to the present invention were synthesized:

1) 12-Methyl-2-tetradecenoic acid
2) 11-Methyl-dodeca-2,4-dienoic acid
3) 13-Methyl-9-tetradecene acid
4) 12-Ethyl-12-tridecenoic acid
5) 3,11-Dimethyl-dodecanoic acid
6) 9-Ethyl-11-methyl-dodecanoic acid
7) 9-Hydroxy-11-methyl-dodecanoic acid
8) 2-Amino-11-methyl-dodecanoic acid
9) 9-Mercapto-11-methyl-dodecanoic acid
10) 9-Oxo-11-methyl-dodecanoic acid
11) 9-Hydroxyimino-11-methyl-dodecanoic acid
12) 3-Chloro-11-methyl-dodecanoic acid
13) 9-Carboxymethylamino-11-methyl-dodecanoic acid
14) 2-Glucosamino-11-methyl-dodecanoic acid
15) 4-(8-Methyl-nonyl)-5-carboxy-tetrahydroimidazoyl-2-one
16) 7-(6N-Adenyl)-9-methyl-decanoic acid
17) 11-Methyl-9-oxo-dodecyl (3,4,5-trihydroxy)benzoate
18) 13-Methyl-3-oxo-tetradecanal
19) Sodium 1-hydroxy 3-oxo-15-methyl-hexadecyl-sulfonate
20) N-(-13-Methyl-tetradecanoyl)-2-amino-7-ribo purine
21) 2N-(13-Methyl-tetradecanoyl)-guanosine
22) 2N-(13-Methyl-tetradecanoyl)guanine
23) 6N-(11-Methyl-dodecanoyl)adenine
24) N,N-Diethyl-10-methylundecylamine
25) N,N-di(2-aminoethyl)-12-methyl-tridecylamine trihydrochloride
26) 13-Methyl-tetradecanal-N-hydroxyimine
27) N-4-Carboxy-benzyl-(11-methyl-3-oxo-dodecyl) imine
28) 2-(10-Methyl-undecyl)-adenine hydrochloride
29) 2-(9-Methyl-decyl)-adenine
30) 2-(11-Methyldodecyl)-4-amino-pyrimidine hydrochloride
31) Sodium 2-(5-hydroxy-1-imidazolyl)-11-methyl-dodecanoate
32) 12-methyl-1,10-tridecanediol
33) 6-[(N-11-Methyl-dodecanoyl)glycyl]thymine
34) 13-Methyl-tetradecyl urea
35) (11-Methyl-9-hydroxy-dodecyl)ethyl ether
36) 12-Methyl-3-oxo-tridecyl-3,4,5-trihydroxy benzoate
37) 1-(2-Chloroethyl)-1-nitroso-3-(12-methyl-tridecyl) urea
38) N-4-Methyl-benzenesulfonyl-13-Methyl-tetradecyl amine
39) (5-Carboxy-2,3,-dihydroxy phenyl)13-methyl-tetradecanoate
40) 6N-13-methyl-tetradecyl-5-flucytosine
41) 6N-(13-Methyl-tetradecanoyl)adenosine
42) 1N-(13-methyl-tetradecanoyl)-5-fluoropyrimidine-2,4-dione
43) N,N-Di(2-chloroethyl)-4-(13-methyl-tetradecyl) aniline
44) 2-(2,4-Dihydroxyphenyl)-13-methyl tetradecanoic acid
45) N-(12-methyl-tridecyl)hydrazine hydrochloride
46) 10-Methoxy-12-methyl-tridecanol
47) (12-Methyl-tridecyl)-2,4-dimethoxy benzene
48) 12-Methyl-3-oxo-tridecyl-3,4,5-trimethoxy-benzoate
49) (5-Carboxy-2,3-dimethoxy phenyl)13-methyl-tetradecanoate The in vitro anti-cancer efficacy tests of all the compounds above were carried out in various human cancer cell lines including leukemia K562, NPC D562, small-cell lung cancer EKVX, colon cancer HCT116, CNS cancer SF-268, melanoma SK-MEL-5, ovarian cancer IGROV1, renal cancer RFX 393, prostate cancer DU-145, breast cancer MCF7, lung cancer H1688, liver cancer SNU-423, and pancreas cancer CRL-1687. After treatment with the test compounds and solvent control, the numbers of live cells were counted by trypan blue dye exclusion, and $IC_{90}$ for various cancer cell lines were calculated, ranging from 2.1 mg/ml to 49.3 mg/ml.

N-(12-methyl-tridecyl)hydrazine hydrochloride, one of the compounds above, was used to test the possible preventing cancer effects on mice, including breast cancer, prostate cancer, stomach cancer, lung cancer and skin cancer. More or less prevention effects were found in the tests, with rate from 30% up to 70%. The most significant effects were observed in preventing skin cancer.

Experiment 2 N-(12-methyl-tridecyl)hydrazine hydrochloride's Function in Preventing Ultraviolet B Ray (UVB)-Induced Skin Cancer N-(12-methyl-tridecyl)hydrazine hydrochloride (Sample) was resolved with 0.8% Tween resulting in a final concentration of 10%.

Forty female SKH-1 hairless mice were randomly divided into control and test groups of 20 each. Each mouse in both groups was treated topically once with DMBA (5.12 μg dissolved in 200 μl acetone solution) to achieve tumor initiation. One week later (day 8), animals in test group started to receive topical application of 200 μl. Sample solution once a day. The control group received 200 μl Tween 80 solvent instead every day. Thirty minutes after the application, animals in both groups were exposed to UVB (290–320 nm) radiation at the dosage of 180 mJ/cm$^2$ per day to induce growth of tumor. The animals were evaluated for tumor development at the end of 30 weeks.

The results suggest that the Sample has a preventive effect when used during early stage of tumor induction. At the end of the experiment, the animals in the Sample-treated group showed a 45% reduction in tumor incidence compared to those in the control group. The average size of cancer in the Sample-treated group was also 85% smaller.

The compounds with the specific structure disclosed in the present invention, including, but not limited to, N-(12- methyl-tridecyl)hydrazine hydrochloride, have a cancer prevention function, including for skin cancer, breast cancer, prostate cancer, stomach cancer and lung cancer.

Experiment 3 Influence of N-(12-methyl-tridecyl)hydrazine hydrochloride (Sample) on Immune Functions 1: Phagocytic Function of Reticuloendothelial System 50 female ICR strain mice, weighing 19–24 g, were randomly divided into 5 groups of 10 each. One group was given N.S. at 20 ml/kg i.g. as a normal control. A positive control group was given CTX i.g. at 25 mg/kg on day 1 and 6. A third group was given N-(12-methyl-tridecyl-hydrazine hydrochloride (Sample) only at 400 mg/kg i.g. The remaining two groups were given both CTX (25 mg/kg on day 1 and 6) and Sample (100 mg/kg and 400 mg/kg, respectively). All treatments except CTX were administered daily for 9 days. 30 minutes after the last administration, 0.15 ml Yidege (1:10) was injected into the tail vein of each mouse. 1 minute and 5 minutes after, blood was drawn and 20 μl serum was mixed with 0.1% $Na_2CO_3$. $OD_{680}$ was measured and the clearance index $K=(1\ gOD_1-1\ gOD_2)/(t_2-t_1)$ was calculated. The results were subject to t test and shown in Table 1.

TABLE 1

Effects of Sample on Serum Clearance Index of Carbon Grain in Normal and Immune-compromised Mouse

| Group (i.g.) | No. of mice | K (X ± SD) | P Compared with Group1 | P Compared with Group2 |
|---|---|---|---|---|
| N.S. 0.2 ml/10 g | 10 | 0.0763 ± 0.0335 | | <0.001 |
| CTX 25 mg/kg | 10 | 0.0260 ± 0.0116 | <0.001 | |
| Sample 400 mg/kg | 10 | 0.0792 ± 0.0230 | >0.05 | <0.001 |
| Sample 100 mg/kg + CTX 25 mg/kg | 10 | 0.0433 ± 0.0401 | <0.001 | <0.001 |
| Sample 400 mg/kg + CTX 25 mg/kg | 10 | 0.0603 ± 0.0371 | <0.001 | <0.001 |

The results in Table 1 demonstrate that N-(12-methyl-tridecyl)hydrazine hydrochloride (Sample) had no obvious effect on the Clearance Index of Carbon grain in normal mouse ($P_{1,3}>0.05$). Moreover the Sample could even improve the clearance of Carbon grain in CTX-treated mouse to a certain extent (both $P_{2,4}$ and $P_{2,5}<0.01$).

2: Serum Hemolysinogenesis 50 male ICR strain mice, weighing 20–23 g, were randomly divided into 5 groups of 10 each. The method of administration in each group was the same as above (phagocytic function). However, on the 6th day after administration, 0.2 ml 3:5 (V/V) sheep red blood cell (RBC) suspension was injected i.p. into each mouse. 4 days later (day 10), blood was drawn from all animals and serum was prepared and then diluted 600 times. 1 ml diluted serum was mixed with 0.5 ml 10% sheep RBC suspension. N.S. was used as blank control. All samples were incubated at 37° C. for 30 minutes, and centrifuged (2000 rev/min) for 5 minutes. The supernatant was collected for measurement of $OD_{540}$ and $HC_{50}$ was calculated. The results were subject to t test and are shown in Table 2.

TABLE 2

Effects of Sample on Serum Hemolysinogenesis in Normal and Immune-compromised Mouse

| Group (i.g.) | No. of Mice | $HC_{50}$ (X ± SD) | P Compared with Group1 | P Compared with Group2 |
|---|---|---|---|---|
| N.S. 0.2 ml/10 g | 10 | 34.91 ± 2.32 | | <0.001 |
| CTX 25 mg/kg | 10 | 21.83 ± 4.29 | <0.001 | |
| Sample 0.4 g/kg | 10 | 32.08 ± 5.06 | >0.05 | <0.001 |
| Sample 0.1 g/kg + CTX 25 mg/kg | 10 | 22.45 ± 4.12 | <0.001 | >0.05 |
| Sample 0.4 g/kg + CTX 25 mg/kg | 10 | 24.01 ± 3.87 | <0.001 | >0.05 |

The results in Table 2 show that N-(12-methyl-tridecyl)hydrazine hydrochloride (Sample) had no obvious effects on serum hemolysinogenesis in either normal or immune-compromised mouse ($P_{1,3}$, $P_{2,4}$, and $P_{2,5}>0.05$). This suggests that the Sample does not evidently affect host humoral immunity.

3: Weights of Immune Organs

The mice were sacrificed after the Serum hemolysinogenesis test above and the thymus and pancreas were collected and weighed. Indices of each organ (mg/10 g body weight) were calculated and subject to t test, and shown in Table 3 as well.

TABLE 3

Effect of the Sample on the indices of immune organs of both normal and CTX-compromised mice

| Drug (i.g.) | Number of mice | Indices of thymus (mg/10 g avoirdupois) | Indices of pancreas (mg/10 g avoirdupois) |
|---|---|---|---|
| N.S. 0.2 ml/10 g | 10 | 3.832 ± 1.904[a] | 4.607 ± 0.883[a] |
| CTX 25 mg/kg | 10 | 1.296 ± 0.665 | 2.154 ± 1.189 |
| Sample 0.4 g/kg | 10 | 3.617 ± 1.334[a] | 4.541 ± 0.508[a] |
| Sample 0.1 g/kg + CTX 25 mg/kg | 10 | 2.448 ± 0.603[a] | 2.459 ± 0.799 |
| Sample 0.4 g/kg + CTX 25 mg/kg | 10 | 3.307 ± 0.721[a] | 3.506 ± 1.223 |

[a]$P < 0.001$, compared to the control group.

The results in Table 3 show that there was no significant effect of N-(12-methyl-tridecyl)hydrazine hydrochloride on the indices of immune organs for normal mice (both thymus and pancreases, $P_{1,3}>0.05$). As to the mice that were treated by CTX, these indices increased after combined administration of the Sample. The increase in the indices of thymus among these three groups is statistically significant ($P_{1,2}$ and $P_{2,4}<0.001$). It is suggested that N-(12-methyl-tridecyl)hydrazine hydrochloride is different from the anticancer compounds of common clinical use, in that it does not inhibit host immune function at therapeutic dosage.

Similarly, it was shown that the specific structured compounds disclosed in the present invention have no influence on the immune function of the normal body and would not aggravate the immune suppression induced by chemotherapy drugs. Furthermore they have immune boosting effects and alleviate the immune suppression when used in combination with other chemotherapy drugs.

Experiment 4 Influence of N-(12-methyl-tridecyl)hydrazine hydrochloride (Sample) on Mouse Sarcoma $S_{180}$ model 50 female ICR strain mice, weighing 19–22 g, were randomly divided into 5 groups of 10 each. $S_{180}$ sarcoma mass (about 2 mm³ each) was transplanted subcutaneously into the right armpits of all animals following standard procedure. 3 test groups were given N-(12-methyl-tridecyl)hydrazine hydrochloride (Sample) at 0.1, 0.2, and 0.4 g/kg intragastrically (i.g.) daily for 11 days. The positive control group was given a single dose of cytoxan (CTX) i.g. (25 mg/kg) on day 1. The negative control group was given 0.8% Tween 80 at 0.4 ml/10 g daily for 11 days. On the 12th day, all mice were sacrificed and the tumor was isolated and weighed. The rate of inhibition of tumor growth was calculated and subject to t-test. The results are shown in Table 4.

TABLE 4

Inhibition of growth of mouse sarcoma $S_{180}$ by Sample

| Group | No. of Mice | Body Weight (g, X ± SD) before treatment | Body Weight (g, X ± SD) after treatment | Tumor Weight (g, X ± SD) | Inhibition Rate (%) |
|---|---|---|---|---|---|
| 0.8% Tween 80. 20 ml/kg | 10 | 21.8 ± 1.4 | 26.6 ± 1.8 | 1.10 ± 0.31 | — |
| Sample 100 mg/kg | 10 | 21.9 ± 1.4 | 26.6 ± 1.8 | 0.70 ± 0.12[b] | 36.36 |
| Sample 200 mg/kg | 10 | 21.9 ± 1.3 | 25.7 ± 1.7 | 0.41 ± 0.10[b] | 62.73 |
| Sample 400 mg/kg | 10 | 21.8 ± 1.3 | 25.0 ± 1.3 | 0.33 ± 0.10[b] | 70.00 |
| CTX 25 mg/kg (Positive Control) | 10 | 21.8 ± 1.5 | 25.6 ± 1.6 | 0.31 ± 0.11[b] | 71.82 |

[b]$P < 0.001$, compared to the control group.

Similarly, it was shown that the specific structured compounds disclosed in present invention have significant anticancer activity on human or animal like N-(12-methyl-tridecyl)hydrazine hydrochloride does.

Experiment 5 Influence of 12-methyl-2-tetradecenoic Acid (Sample) on Inflammation 12-Methyl-2-tetradecenoic acid in an oil state was directly applied on the focus surface of oral or tongue to patients of oral adnoma and tongue cancer. It was recorded that about one week later, the focus reduced, swelling disappeared, and the patients might swallow food.

12-Methyl-2-tetradecenoic acid in an oil state was directly applied on the inflamed surface of patients with body skin ulcerous wounds. It was also recorded that compared to common anti-inflammatory cream, 12-Methyl-2-tetradecenoic acid has a better anti-inflammation function and the ulcerous wound healed quickly, indicating the anti-inflammation effects on humans.

The compounds with the specific structure in the present invention, whether chemically synthesized, or obtained through a fermentation process using a microorganism, or extracted from natural resources, or administered in a natural mixture without extraction, have significant anti-cancer activity, preventing cancer, and immune boosting and anti-inflammation effects on humans and animals. These compounds can also be taken orally or by injection, in the forms of liquid, powder, tablet, injection, capsule, or encapsulated liposome, or they can be topically applied in the forms of cream, ointment, or lotion.

The invention claimed is:

1. A compound having a formula selected from the group consisting of the following formulae (6) and (8) through (12):

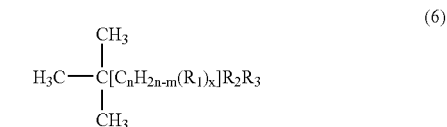

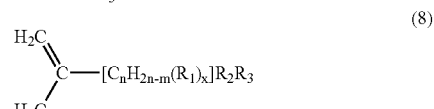

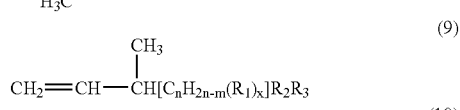

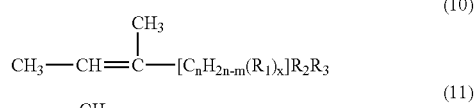

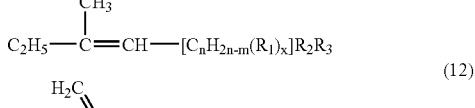

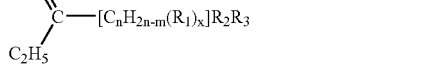

wherein n is an integer from 5 to 19, m is an integer from 0 to 2b+x, inclusive, wherein b is the maximum number of unsaturated bonds, and wherein a double bond is assigned as 1 and a triple bond is assigned as 2, and $R_1$, $R_2$, and $R_3$, are chemically possible groups to form the structures above, provided that $R_2R_3$ is a polar moiety, x is the number of $R_1$ groups (same or different) at any possible position (x is an integer $\leq 2n-m$), and the salt thereof, and provided that when the compound has formula (6), m is 0, and $(R_1)_x$ are all hydrogen when x is not 0, then $R_2R_3$ is not carboxyl.

2. The compound of claim 1, wherein $R_1$ is selected from the group consisting of (1) hydrogen, (2) methyl group, (3) ethyl group, (4) hydroxyl group, (5) amino group, (6) mercapto group, (7) oxo group, (8) imino group, (9) halogen, (10) amino acid, (11) amino-glucose, (12) heterocyclic group and substituted heterocyclic group, (13) methoxy, (14) ethoxy, and (15) acetyloxy.

3. The compound of claim 1, wherein $R_2$ is selected from the group consisting of (1) alkoxylene group, (2) carbonyl group, (3) amine group, (4) imine group, and (5) substituted or unsubstituted phenyl group, or substituted or unsubstituted heterocyclic group, including the salt thereof.

4. The compound of claim 1, wherein $R_3$ is selected from the group consisting of (1) hydrogen, (2) hydroxyl group, (3) amine group, $NR_4R_5$, (4) methyl group and ethyl group, (5) acyl group, —$COR_4$, (6) sulfonyl group, —$SO_2R_4$, (7) hydroxyl-, halogen-, halide-, carboxyl-, carbonyl-, amino-, or glucosyl-substituted phenyl group or heterocyclic group, and (8) hydrazine group, wherein the $R_4$ and $R_5$ groups are independently, the following: hydrogen, methyl, ethyl, chloroethyl, ethoxyl, or hydroxyl, or hydroxyl-, halogen-, halide-, carboxyl-, carbonyl-, amino-, or glucosyl-substituted phenyl group or heterocyclic group, wherein $R_4$ and $R_5$ can also form a heterocyclic ring with N, and wherein the hydroxyl group in (2) or (7) can be replaced with methoxy (—OCH₃), ethyloxy (—OC₂H₅), or acetyloxy (—OCOCH₃) group.

5. A compound selected from the group consisting of:
11-Methyl-dodeca-2,4-dienoic acid,
13-Methyl-9-tetradecene acid,
12-Ethyl-12-tridecenoic acid,
9-Ethyl-11-methyl-dodecanoic acid,
9-Hydroxy-11-methyl-dodecanoic acid,
2-Amino-11-methyl-dodecanoic acid,
9-Mercapto-11-methyl-dodecanoic acid,
9-Oxo-11-methyl-dodecanoic acid,
9-Hydroxyimino-11-methyl-dodecanoic acid,
3-Chloro-11-methyl-dodecanoic acid,
9-Carboxymethylamino-11-methyl-dodecanoic acid,
2-Glucosamino-11-methyl-dodecanoic acid,
4-(8-Methyl-nonyl)-5-carboxy-tetrahydroimidazoyl-2-one,
7-(6N-Adenyl)-9-methyl-decanoic acid,
11-Methyl-9-oxo-dodecyl(3,4,5-trihydroxy)benzoate,
13-Methyl-3-oxo-tetradecanal,
Sodium 1-hydroxy 3-oxo-15-methyl-hexadecyl-sulfonate,
N-(-13-Methyl-tetradecanoyl)-2-amino-7-ribo purine,
2N-(13-Methyl-tetradecanoyl)-guanosine,
2N-(13-Methyl-tetradecanoyl)guanine,
6N-(11-Methyl-dodecanoyl)adenine,
N,N-Diethyl-10-methylundecylamine,
N,N-di(2-aminoethyl)-12-methyl-tridecylamine tri-hydrochloride,
13-Methyl-tetradecanal-N-hydroxyimine,
N-4-Carboxy-benzyl-(11-methyl-3-oxo-dodecyl)imine,
2-(10-Methyl-undecyl)-adenine hydrochloride,
2-(9-Methyl-decyl)-adenine,
2-(11-Methyldodecyl)-4-amino-pyrimidine hydrochloride,
Sodium 2-(5-hydroxy-1-imidazolyl)-11-methyl-dodecanoate,
12-methyl-1,10-tridecanediol,
6-[(N-11-Methyl-dodecanoyl)glycyl]thymine,
13-Methyl-tetradecyl urea,
(1-Methyl-9-hydroxy-dodecyl)ethyl ether,
12-Methyl-3-oxo-tridecyl-3,4,5-trihydroxy benzoate,
1-(2-Chloroethyl)-1-nitroso-3-(12-methyl-tridecyl)urea,
N-4-Methyl-benzenesulfonyl-13-Methyl-tetradecyl amine,
(5-Carboxy-2,3,-dihydroxy phenyl)13-methyl-tetradecanoate,
6N-13-methyl-tetradecyl-5-flucytosine,
6N-(13-Methyl-tetradecanoyl)adenosine,
1N-(13-methyl-tetradecanoyl)-5-fluoropyrimidine-2,4-dione,
N,N-Di(2-chloroethyl)-4-(13-methyl-tetradecyl)aniline,
2-(2,4-Dihydroxyphenyl)-13-methyl tetradecanoic acid,
N-(12-methyl-tridecyl)hydrazine hydrochloride,
10-Methoxy-12-methyl-tridecanol,
(12-Methyl-tridecyl)-2,4-dimethoxy benzene,
12-Methyl-3-oxo-tridecyl-3,4,5-trimethoxy-benzoate, and
(5-Carboxy-2,3-dimethoxy phenyl)13-methyl-tetradecanoate.

6. The compound of claim 5, which is N-(12-methyl-tridecyl) hydrazine hydrochloride.

7. A method of treating inflammation comprising applying a compound having a formula selected from the group consisting of the following formulae (4) through (12):

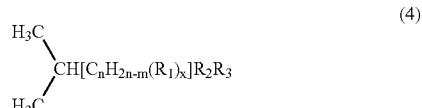

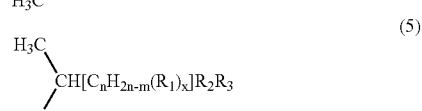

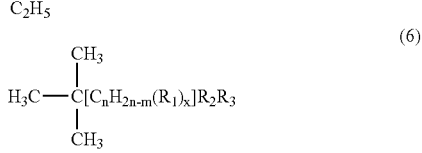

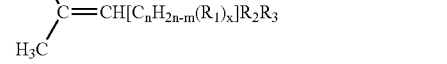

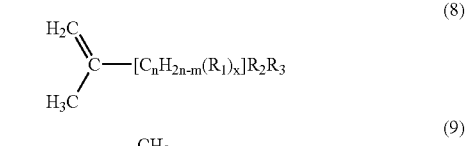

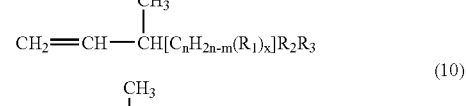

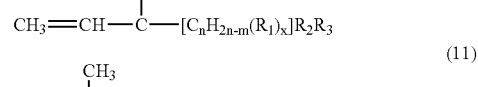

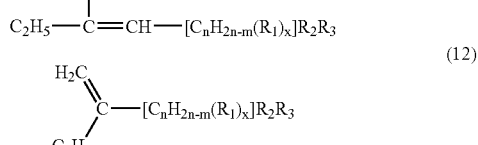

wherein n is an integer from 5 to 19, m is an integer from 0 to 2b+x, inclusive, wherein b is the maximum number of unsaturated bonds, and wherein a double bond is assigned as 1 and a triple bond is assigned as 2, and $R_1$, $R_2$, and $R_3$, are chemically possible groups to form the structures above, provided that $R_2R_3$ is a polar moiety, x is the number of $R_1$ groups (same or different) at any possible position (x is an integer $\leq 2n-m$), and the salt thereof.

8. The method of claim 7, wherein the compound is 12-methyl-2-tetradecenoic acid.

9. A compound having a formula (7):

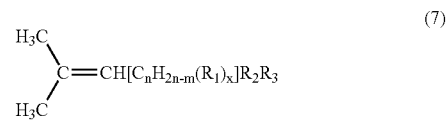

wherein n is an integer from 5 to 19, m is an integer from 0 to 2b+x, inclusive, wherein b is the maximum number of unsaturated bonds, and wherein a double bond is assigned as 1 and a triple bond is assigned as 2, and $R_1$, $R_2$, and $R_3$, are chemically possible groups to form the structures above, provided that $R_2R_3$ is a polar moiety, x is the number of $R_1$ groups (same or different) at any possible position (x is an integer $\leq 2n+m$), and the salt thereof, provided that when $R_2R_3$ contains a heterocyclic group, it is a nitrogen-containing heterocyclic group.

10. The compound of claim 9, wherein $R_1$ is selected from the group consisting of
   (1) hydrogen, (2) methyl group, (3) ethyl group, (4) hydroxyl group, (5) amino group, (6) mercapto group, (7) oxo group, (8) imino group, (9) halogen, (10) amino acid, (11) amino-glucose, (12) heterocyclic group and substituted heterocyclic group, (13) methoxy, (14) ethoxy, and (15) acetyloxy.

11. The compound of claim 10, wherein $R_2$ is selected from the group consisting of
   (1) alkoxylene group, (2) carbonyl group, (3) amine group, (4) imine group, and (5) substituted or unsubstituted phenyl group, or substituted or unsubstituted nitrogen-containing heterocyclic group, including the salt thereof.

12. The compound of claim 10, wherein $R_3$ is selected from the group consisting of
   (1) hydrogen, (2) hydroxyl group, (3) amine group, $NR_4R_5$, (4) methyl group and ethyl group, (5) acyl group, —$COR_4$, (6) sulfonyl group, —$SO_2R_4$, (7) hydroxyl-, halogen-, halide-, carboxyl-, carbonyl-, amino-, or glucosyl- substituted phenyl group or nitrogen-containing heterocyclic group, and (8) hydrazine group, wherein the $R_4$ and $R_5$ groups are independently, the following: hydrogen, methyl, ethyl, chloroethyl, ethoxyl, or hydroxyl, or hydroxyl-, halogen-, halide-, carboxyl-, carbonyl-, amino-, or glucosyl-substituted phenyl group or nitrogen-containing heterocyclic group, wherein $R_4$ and $R_5$ can also form a heterocyclic ring with N, and wherein the hydroxyl group in (2) or (7) can be replaced with methoxy (—$OCH_3$), ethyloxy (—$OC_2H_5$), or acetyloxy (—$OCOCH_3$) group.

* * * * *